United States Patent [19]

Laurenzo

[11] Patent Number: 5,166,434

[45] Date of Patent: Nov. 24, 1992

[54] PROCESS FOR THE PREPARATION OF AROMATIC-SUBSTITUTED UNSATURATED AMIDES

[75] Inventor: Kathleen S. Laurenzo, Baton Rouge, La.

[73] Assignee: Ethyl Corporation, Richmond, Va.

[21] Appl. No.: 677,989

[22] Filed: Apr. 1, 1991

[51] Int. Cl.$^5$ .......................................... C07C 233/08
[52] U.S. Cl. ........................................ 564/161; 558/6; 564/163; 564/166; 564/167; 564/169; 564/170; 564/171; 564/172; 564/180; 564/182; 564/205
[58] Field of Search .............. 564/161, 182, 205, 163, 564/166, 167, 170, 171, 172, 169, 180; 558/6

[56] References Cited

U.S. PATENT DOCUMENTS 3,478,105  11/1969  Kuderna, Jr. et al. ............. 564/162
3,513,186  5/1970  Kuderma, Jr. et al. ............. 558/388

OTHER PUBLICATIONS

March, J., Advanced Organic Chemistry, John Wiley & Sons, pp. 901–902 (1985).
McClelland, "$A_{A1}2$ Hydrolysis of 2,6-Dimethylbenzimidate Esters", JACS, vol. 97(11), pp. 3177–3181, (1975).

Primary Examiner—Glennon H. Hollrah
Assistant Examiner—Scott C. Rand
Attorney, Agent, or Firm—Richard J. Hammond

[57] ABSTRACT

A process is disclosed for preparing aromatic-substituted unsaturated amides. The process comprises treating a compound of the formula

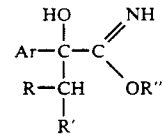

where Ar is $C_6$ to $C_{10}$ aryl unsubstituted or substituted with at least one halo, amino, nitro, hydroxy, $C_1$ to $C_{12}$ linear or branched alkyl, $C_1$ to $C_{12}$ linear or branched alkoxy or haloalkyl, the alkyl moiety being $C_1$ to $C_6$ linear or branched or the group

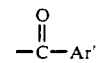

where Ar' is $C_6$ to $C_{10}$ aryl unsubstituted or substituted with at least one halo, amino, nitro, hydroxy, $C_1$ to $C_{12}$ linear or branched alkyl, $C_1$ to $C_{12}$ alkoxy or haloalkyl, the alkyl moiety being $C_1$ to $C_6$ linear or branched; and R and R' are the same or different and are hydrogen or $C_1$ to $C_{12}$ linear or branched alkyl and can also be phenyl unsubstituted or substituted with at least one halo, amino, nitro, hydroxy, $C_1$ to $C_{12}$ linear or branched alkyl, $C_1$ to $C_{12}$ linear or branched alkoxy or haloalkyl, the alkyl moiety being $C_1$ to $C_6$ linear or branched, with an inorganic dehydrating agent.

9 Claims, 1 Drawing Sheet

PROCESS FOR THE PREPARATION OF AROMATIC-SUBSTITUTED UNSATURATED AMIDES

FIELD OF THE INVENTION

This invention relates to a method for preparing aromatic-substituted acrylamides. More particularly, this invention relates to treating aromatic-substituted hydroxy imidates with reagents that produce aromatic-substituted acrylamides. These amides are intermediates for "profen" type compounds.

BACKGROUND OF THE INVENTION

The dehydration of alcohols to form ethers and/or olefins is well known. These reactions are readily accomplished by using sulfuric or phosphoric acid, methods applied successfully to such high molecular weight alcohols as 1-dodecanol. However, because of the prevalence of side reactions, e.g., rearrangement, the olefin producing reactions are not as widely applicable as those where such by-product formation is minimized. Thus, a variety of metal oxides, such as aluminum oxide, chromium (III) oxide, titanium oxide and tungsten oxide, have been successfully employed in such dehydrations, as have sulfides, other metallic salts and zeolites. Other dehydrating agents include phosphorous pentoxide, potassium acid sulfate and anhydrous copper (II) sulfate. See, for example, page 902, March, et al., *Advanced Organic Chemistry*, 3rd Edition, 1985.

Conventionally, acids can be readily converted to their amides by the action of ammonia on their ester, acid chloride or anhydride derivatives. The hydrolysis of nitriles to carboxylic acids is known to proceed through an isolable amide intermediate, the tautomer of such amide being a hydroxyimine. No facile preparation of unsaturated amides has been reported. However, see U.S. Pat. No. 3,478,105 and 3,513,186. Accordingly, there is unsaturated amides such as 2-(4-isobutylbenzene)acrylamide.

DETAILED DESCRIPTION OF THE PREFERRED EMBODIMENTS

Figure 1:
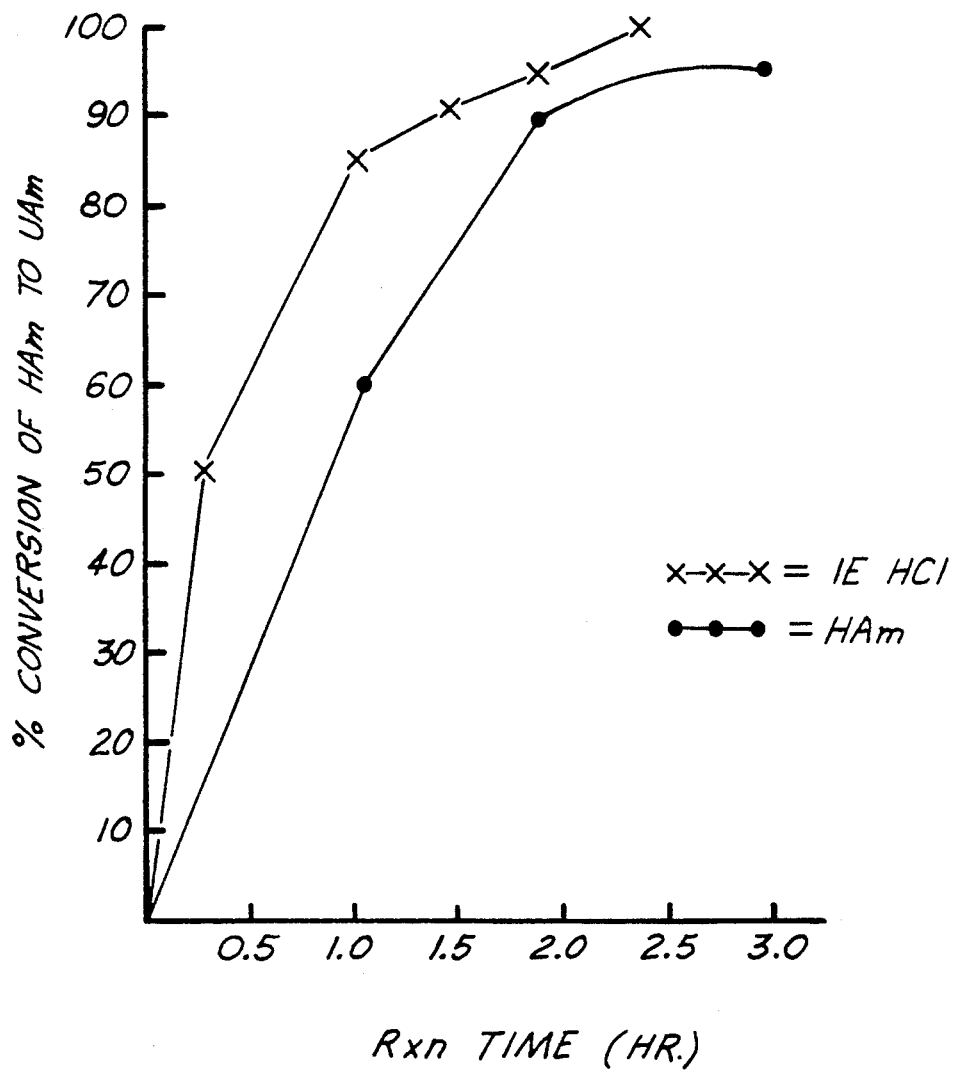
FIG. 1 is a plot comparing the rate of conversion of 2-hydroxy-2-(4-isobutylbenzene)propionamide and its corresponding iminoester into 2-(4-isobutylbenzene)acrylamide.

In the present specification, alkyl means straight or branched chain alkyl having 1 to 12 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, and dodecyl.

Substituted aryl means aryl (phenyl, naphthyl, etc.) unsubstituted, or substituted by at least one substituent selected from the group consisting of halogen (chlorine, bromine, fluorine or iodine), amino, nitro, hydroxy, alkyl, alkoxy which means straight or branched chain alkoxy having 1 to 12 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halogen, and includes, for example, chloromethyl, bromomethyl, fluoromethyl, iodomethyl, 2-chlorethyl, 2-bromoethyl, 2-fluorethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

The process of the present invention is a single step reaction resulting in the preparation of a compound of the formula

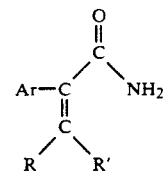   I where Ar is $C_6$ to $C_{10}$ aryl unsubstituted or substituted with at least one substituent selected from the group consisting of halo, amino, nitro, hydroxy, $C_1$ to $C_{12}$ linear or branched alkyl, $C_1$ to $C_{12}$ alkoxy, haloalkyl, said alkyl moiety being $C_1$ to $C_6$ linear or branched alkyl, and

where Ar' is $C_6$ to $C_{10}$ aryl unsubstituted or substituted with at least one substituent selected from the group consisting of halo, amino, nitro, hydroxy, $C_1$ to $C_{12}$ linear or branched alkyl, $C_1$ to $C_{12}$ alkoxy, haloalkyl, said alkyl moiety being $C_1$ to $C_6$ linear or branched alkyl; and R and R' are the same or different and are hydrogen, or $C_1$ to $C_6$ linear or branched alkyl.

Preferably, the compounds prepared by the process of the present invention are those where R and R' are the same, most preferably being hydrogen.

In the above preferred and particularly preferred compounds, Ar is preferably phenyl or naphthyl unsubstituted or substituted with at least one substituent selected from the group consisting of halo, $C_1$ to $C_6$ linear or branched alkyl and $C_1$ to $C_6$ linear or branched alkyl on the group

phenyl. Particularly preferred is phenyl substituted with methyl, ethyl, n-propyl or secondary butyl or naphthyl substituted with methoxy or ethoxy.

The process of this invention involves the treatment of compounds of the formula

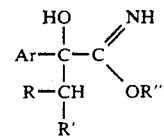   II where Ar is $C_6$ to $C_{10}$ aryl unsubstituted or substituted with at least one substituent selected from the group consisting of halo, amino, nitro, hydroxy, $C_1$ to $C_{12}$ linear or branched alkyl, $C_1$ to $C_{12}$ linear or branched alkoxy or haloalkyl, said alkyl moiety being $C_1$ to $C_6$ linear or branched alkyl and

where Ar' is $C_6$ to $C_{10}$ aryl unsubstituted or substituted with at least one substituent selected from the group consisting of halo, amino, nitro, hydroxy, $C_1$ to $C_{12}$ linear or branched alkyl, $C_1$ to $C_{12}$ alkoxy, haloalkyl, said alkyl moiety being $C_1$ to $C_6$ linear or branched alkyl; R, R' and R'' are the same or different and are hydrogen or $C_1$ to $C_{12}$ linear or branched alkyl with the proviso that R'' is never hydrogen and can be phenyl unsubstituted or substituted with at least one substituent selected from the group consisting of halo, amino, nitro, hydroxy, $C_1$ to $C_6$ linear or branched alkyl, $C_1$ to $C_6$ linear or branched alkoxy and haloalkyl, the alkyl moiety being $C_1$ to $C_6$ linear or branched alkyl.

The reagents employed to accomplish the preparation of the aromatic-substituted aliphatic amides (the compounds of Formula I) are inorganic dehydrating agents. Surprisingly, the usual protonic dehydrating agents, such as sulfuric or phosphoric acid, are not effective in accomplishing this reaction. Reactions with these materials result in low or no yields of the desired compounds of Formula I. The preferred dehydrating agents are those compounds illustrated by phosphorus pentoxide, zinc chloride, boron trifluoride-etherate, potassium acid sulfate, potassium hydroxide and anhydrous copper (II) sulfate. Most preferred for treating the compounds of Formula II to produce compounds of Formula I is the compound potassium acid sulfate, particularly in the anhydrous and fused form.

While the reaction of the present invention appears to follow a standard elimination reaction, the expected product of such elimination (the unsaturated imino ester) is not produced. Using the inorganic dehydrating agents of the present invention, aromatic-substituted amides unexpectedly result in good yields. This is even more surprising given the well-known susceptibility of amides to form ketenimes upon dehydration.

In one embodiment of the present invention, a slurry of the compounds of Formula II is treated with the inorganic dehydrating agent. The solvents employed to produce the slurry are inert organic solvents. Typically, they are polar. Preferably, these solvents comprise optionally substituted aromatic solvents, the substituents being at least one halo, $C_1$ to $C_6$ linear or branched alkyl, $C_1$ to $C_6$ linear or branched alkoxy or nitro; or optionally substituted aliphatic solvents, the substituents being at least one halo or nitro. Preferably the solvents are benzene optionally substituted with at least one halo. Mixtures of the above solvents may also be employed. Most preferably the solvent is o-dichlorobenzene.

The reaction is carried out by forming a slurry of the compounds of Formula II with the inert organic solvent and heating the solution to about 100° C. to about 200° C. in the presence of $KHSO_4$. Usually, the reflux temperature (if within this range) of the solvents is a satisfactory alternative. Preferably the reaction is more readily accomplished at the higher temperature, i.e., 150° C. to 190° C., most preferably 150° C. to 175° C.

Many of the compounds of Formula I will separate as a solid, crystalline precipitate from the reaction solution. In such case, the solid is easily removed by conventional means, i.e., filtration, centrifugation, etc. Where the compounds of Formula I do not separate (are soluble in the reaction solution), removal of some or most of the solvent (evaporation) and cooling will produce the desired precipitate. In any case, separation of the product is accomplished without difficulty.

In a preferred embodiment, methyl 2-hydroxy-2-(4-isobutylbenzene)acetimidate is first converted in situ to 2-hydroxy-2-(4-isobutylbenzene)propionamide (II) which then undergoes dehydration to the 2-(4-isobutylbenzene)acrylamide. Dehydration occurs when starting from 2-hydroxy-2-(4-isobutylbenzene)proprionamide under identical conditions.

The dehydration is facilitated by the initial presence of the iminoester hydrochloride. The dehydration is faster, particularly in the early stages of the reaction, when methyl 2-hydroxy-2-(4-isobutylbenzene)acetimidate is the starting material.

The following examples are exemplary of the process of the present invention.

EXAMPLE 1

Dehydration of Iminoester Hydrochloride

Methyl 2-hydroxy-2-(4-isobutylbenzene)acetimidate (1.6 g, 5.9 mmole) and ortho dichlorobenzene (o-DCB) (16 mL) were added to a 25 mL 2-neck round bottom flask equipped with magnetic stirrer, thermometer, Therm-o-Watch and condenser. Fused $KHSO_4$ (3.3 g) was added and the mixture heated to 150° C. for 4.5 hours. The hot solution was suction filtered to remove $KHSCO_4$ and, upon cooling to room temperature (RT), crystals precipitated. The crystals were filtered and washed with hexane to remove DCB, then suction dried to yield 0.57 g (48%) of 2-(4-isobutylbenzene)-acrylamide, m.p. 157°–158° C. A second crop was obtained by evaporating the filtrate and washing the resulting crystals with hexane, bringing the total yield to 60%.

EXAMPLE 2

The reaction in Example 1 was repeated, and the progress of the reaction was followed by GC. When the temperature reached 100° C., the methyl 2-hydroxy-2-(4isobutylbenzene)acetimidate had been converted to a mixture of 2-hydroxy-2-(4-isobutylbenzene)proprionamide (87%) and corresponding hydroxy methyl ester (10%). After 2.5 hours, the hot solution was suction filtered to remove $KHSO_4$. Upon cooling to RT, crystals precipitated. The reaction mixture was evaporated to dryness and the resulting crystals washed with hexane and suction dried to yield 0.84 g (70%) of 2-(4-isobutylbenzene)acrylamide. 98.9% pure by GC.

The time of the conversion of 2-hydroxy-2-(4-isobutylbenzene)propionamide into 2-(4-isobutylbenzene)acrylamide is shown in FIG. 1 (the curve HAm) compared to the rate of conversion of methyl 2-hydroxy-2-(4-isobutylbenzene)acetimidate hydrochloride.

EXAMPLE 3

Dehydration of 2-hydroxy-2-(4-isobutylbenzene)propionamide

2-Hydroxy-2-(4-isobutylbenzene)propionamide (1.6 g, 7.2 mmole) and o-DCB (16 mL) were added to a 25 mL 2-neck round bottom flask equipped with magnetic stirrer, thermometer, Therm-o-Watch and condenser. Fused $KHSO_4$ (3.3 g) was added and the mixture heated to 150° C. The reaction was followed by GC and the course of the conversion of 2-hydroxy-2-(4-isobutylbenzene)-proprionamide to 2-(4-isobutylbenzene)acrylamide is shown in FIG. 1. After 3.0 hours, the hot solution was suction filtered to remove KHSO$_4$. Upon cooling to RT, crystals precipitated. The reaction mixture was evaporated to dryness and the resulting crystals washed with hexane and suction dried to yield 1.34 g (92%) of 2-(4-isobutylbenzene)acrylamide, m.p. 147.5°–152° C. 97.5% pure by GC.

I claim:

1. A process for preparing aromatic-substituted aliphatic amides comprising treating a solution of an imino ester of the formula

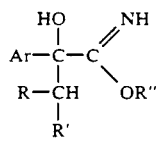

II where Ar is C$_6$ to C$_{10}$ aryl unsubstituted or substituted with at least one substituent selected from the group consisting of halo, amino, nitro, hydroxy, C$_1$ to C$_{12}$ linear or branched alkyl, C$_1$ to C$_{12}$ linear or branched alkoxy, haloalkyl, said alkyl moiety being C$_1$ to C$_6$ linear or branched alkyl and

where Ar' is C$_6$ to C$_{10}$ aryl unsubstituted or substituted with at least one substituent selected from the group consisting of halo, amino, nitro, hydroxy, C$_1$ to C$_{12}$ linear or branched alkyl, C$_1$ to C$_{12}$ alkoxy, haloalkyl, said alkyl moiety being C$_1$ to C$_6$ linear or branched alkyl; R, R' and R'' are the same or different and are hydrogen or C$_1$ to C$_{12}$ linear or branched alkyl with the proviso that R'' is never hydrogen but can also be phenyl unsubstituted or substituted with at least one substituent selected from the group consisting of halo, amino, nitro, hydroxy, C$_1$ to C$_{12}$ linear or branched alkyl, C$_1$ to C$_{12}$ linear or branched alkoxy and haloalkyl, said alkyl moiety being C$_1$ to C$_6$ linear or branched alkyl with potassium acid sulfate and separating from said solution an aromatic substituted aliphatic amide having the formula

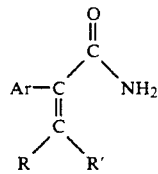

I where Ar, R and R' are as previously defined.

2. The process according to claim 1 wherein the solution uses an inert organic solvent.

3. The process according to claim 2 wherein said inert solvent comprises an optionally substituted aromatic solvent, the substituents being at least one halo, C$_1$ to C$_6$ linear or branched alkyl, C$_1$ to C$_6$ linear or branched alkoxy or nitro, or an optionally substituted aliphatic solvent, the substituents being at least one halo or nitro.

4. The process according to claim 3 wherein said inert solvent is benzene optionally substituted with at least one halo.

5. The process according to claim 1 wherein R, R' and R'' are the same.

6. The process according to claim 1 where R and R' are hydrogen and R'' is C$_1$ to C$_6$ linear or branched alkyl.

7. The process according to claim 6 wherein R'' is methyl.

8. The process according to claim 1 wherein Ar is phenyl, naphthyl unsubstituted or substituted with at least one substituent selected from the group consisting of halo, C$_1$ to C$_6$ linear or branched alkyl and C$_1$ to C$_6$ linear or branched alkoxy or the group

phenyl.

9. The process according to claim 8 wherein Ar is phenyl substituted with methyl, ethyl, n-propyl or secondary butyl or naphthyl substituted with methoxy or ethoxy.

* * * * *